(12) United States Patent
Lutnesky et al.

(10) Patent No.: US 11,065,619 B2
(45) Date of Patent: Jul. 20, 2021

(54) CASSETTES WITH OFFSET VIAS

(71) Applicant: HEWLETT-PACKARD DEVELOPMENT COMPANY, L.P., Spring, TX (US)

(72) Inventors: Gary G. Lutnesky, Corvallis, OR (US); Matthew David Smith, Corvallis, OR (US); Dennis R. Esterberg, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 245 days.

(21) Appl. No.: 16/472,694

(22) PCT Filed: Feb. 3, 2017

(86) PCT No.: PCT/US2017/016514
§ 371 (c)(1),
(2) Date: Jun. 21, 2019

(87) PCT Pub. No.: WO2018/144018
PCT Pub. Date: Aug. 9, 2018

(65) Prior Publication Data
US 2020/0316592 A1    Oct. 8, 2020

(51) Int. Cl.
*B01L 3/00* (2006.01)
*H01R 12/71* (2011.01)
(Continued)

(52) U.S. Cl.
CPC ........... *B01L 3/502715* (2013.01); *B01L 3/02* (2013.01); *B01L 3/502707* (2013.01);
(Continued)

(58) Field of Classification Search
CPC ......... A61L 2209/133; B01L 2200/026; B01L 2200/12; B01L 2300/06; B01L 2300/0645;
(Continued)

(56) References Cited

U.S. PATENT DOCUMENTS

| 9,433,939 B2 | 9/2016 | Duclenhoefer et al. |
| 2004/0053290 A1 | 3/2004 | Terbrueggen et al. |

(Continued)

FOREIGN PATENT DOCUMENTS

| CN | 101095040 A | 12/2007 |
| JP | 2010540934 | 12/2010 |

(Continued)

OTHER PUBLICATIONS

"Multiflo FX Dispenser"; 2015; https://www.biospx.com/dispensers.html.

(Continued)

*Primary Examiner* — Jennifer Wecker
(74) *Attorney, Agent, or Firm* — Fabian VanCott

(57) ABSTRACT

A cassette may include a substrate, a die coupled to the substrate, and an electrical interconnection pad layout formed on a first side of the substrate. The electrical interconnection pad layout may include a first row of interconnect pads including at least one interconnect pad. Each interconnect pad of the first row of interconnect pads may be electrically coupled to one of a first set of vias. The electrical interconnection pad layout may also include a second row of interconnection pads including at least one interconnect pad. Each interconnect pad of the second row of interconnect pads being electrically coupled to one of a second set of vias. The second set of vias electrically coupled to the second row of interconnect pads are offset relative to an alignment of the interconnect pads of the first and second rows.

15 Claims, 13 Drawing Sheets

(51) Int. Cl.
  *H05K 1/11* (2006.01)
  *B01L 3/02* (2006.01)
(52) U.S. Cl.
  CPC ........... *H01R 12/714* (2013.01); *H05K 1/116* (2013.01); *B01L 2200/12* (2013.01); *B01L 2300/06* (2013.01); *B01L 2400/0475* (2013.01); *H05K 2201/094* (2013.01); *H05K 2201/09609* (2013.01)
(58) Field of Classification Search
  CPC .. B01L 2400/0475; B01L 3/02; B01L 3/0268; B01L 3/502; B01L 3/502707; B01L 3/502715; H01R 12/714; G01N 1/00; G01N 2035/0418; G01N 2035/0436; G01N 35/00; G01N 35/1002; G01N 35/1065; H05K 1/116; H05K 2201/094; H05K 2201/09609
  See application file for complete search history.

(56) References Cited

U.S. PATENT DOCUMENTS

| | | |
|---|---|---|
| 2004/0166504 A1 | 8/2004 | Rossier et al. |
| 2006/0007280 A1 | 1/2006 | Ang |
| 2009/0322837 A1 | 12/2009 | Muhl |
| 2010/0244873 A1 | 9/2010 | Dozier, II et al. |
| 2010/0267161 A1 | 10/2010 | Wu et al. |
| 2012/0127239 A1 | 5/2012 | Maruyama |
| 2012/0190589 A1 | 7/2012 | Anderson et al. |
| 2016/0036150 A1* | 2/2016 | Campbell-Brown ........................ B41J 2/17543 439/77 |
| 2016/0129445 A1* | 5/2016 | Corey ............... B01L 3/502715 435/286.1 |

FOREIGN PATENT DOCUMENTS

| | | |
|---|---|---|
| JP | 2014191960 | 10/2014 |
| JP | 2015517849 | 6/2015 |
| JP | 2015534808 | 12/2015 |
| JP | 2016145766 | 8/2016 |
| TW | 200734655 A | 9/2007 |
| WO | WO-2009042631 A2 | 4/2009 |
| WO | WO-2014066704 A1 | 5/2014 |
| WO | WO-2017171801 | 10/2017 |

OTHER PUBLICATIONS

"Walkaway Batch Processing for the Spark™ 10M"; Mar. 2015; Tecan Journal Mar. 2015.

* cited by examiner

CASSETTES WITH OFFSET VIAS

BACKGROUND

An "assay run" is an investigative or analytic event used in, for example, laboratory medicine, pharmacology, analytical chemistry, environmental biology, or molecular biology, for qualitatively assessing or quantitatively measuring the presence, amount, or the functional activity of a sample. The sample may be a drug, a genomic sample, a proteomic sample, a biochemical substance, a cell in an organism, an organic sample, or other inorganic and organic chemical samples. An assay run may measure an intensive property of the sample and express it in the relevant measurement unit such as, for example, molarity, density, functional activity in enzyme international units, degree of some effect in comparison to a standard, among other measurable characteristics. An assay may involve reacting a sample with a number of reagents, and may be classified as an instance of an assay procedure conforming to an assay protocol. An assay protocol may involve a set of reagent and/or sample fluids being dispensed in specific amounts to a number of assay reaction sites such as wells within a well plate. Further, an assay protocol may include additional processing such as mixing, separation, heating or cooling, incubation, and eventually at least one read-out. The reproducibility and run-to-run comparability of an assay depends on the reproduction of its protocol.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements.

DETAILED DESCRIPTION

Figure 1:
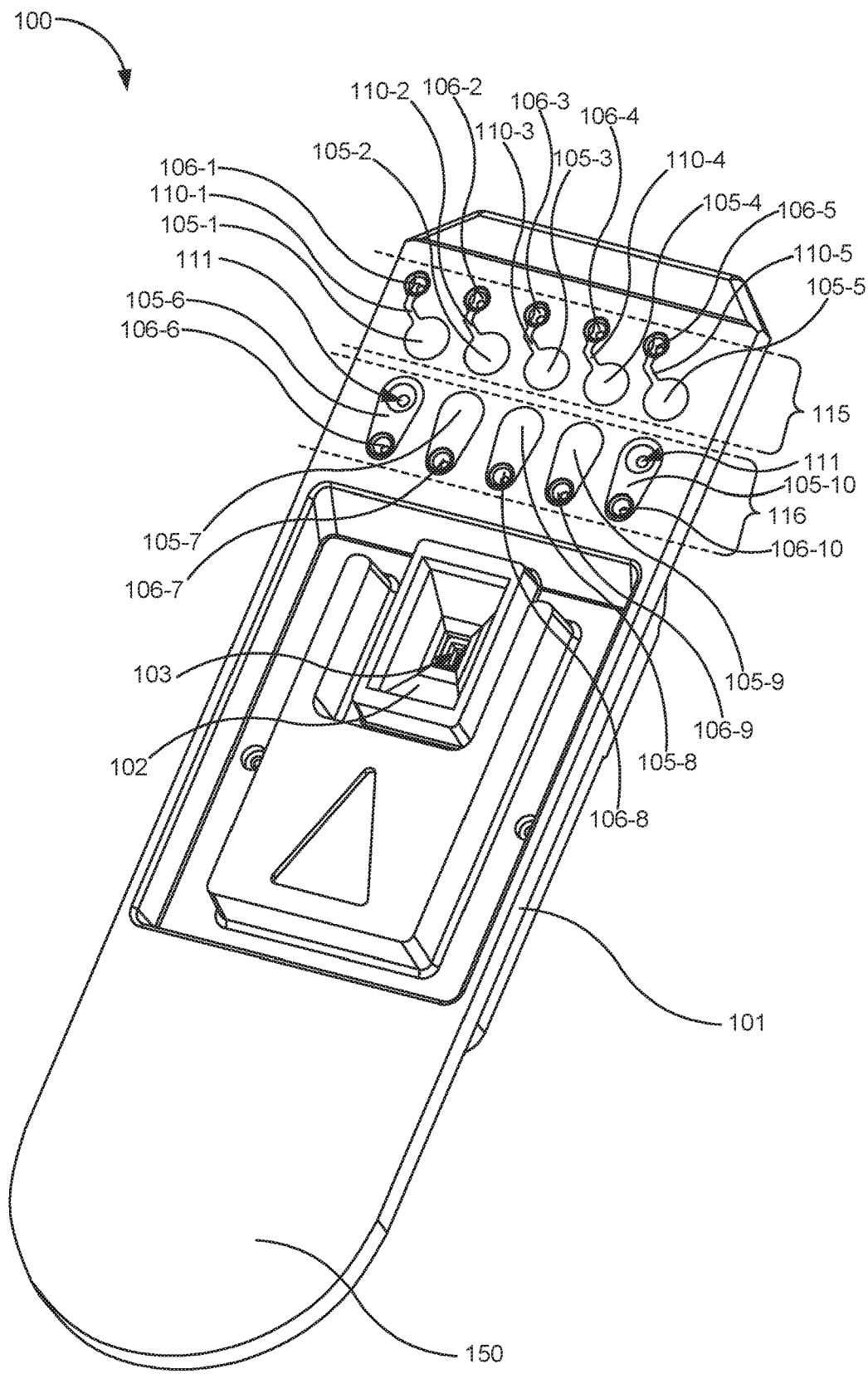
FIG. 1 is a front, perspective view of a first volume cassette, according to one example of the principles described herein.

Some assay fluid dispensing systems may automatically dispense assay fluids such as, for example, samples and reagents, in a precise, controlled fashion into multiple reaction sites called wells within a well plate in a short time. A carefully formulated mixture of several reagents, including a target species of interest, may be carefully formulated at multiple reaction sites for the testing of a set of test sample reagents at multiple concentrations. This allows many reactions to proceed contemporaneously. The automation reduces user effort and user-caused variability, while the concurrency further reduces the time to complete a complex assay.

An assay fluid dispensing system dispense at least one assay fluid such as an analyte or a reagent to the wells in parallel or in series, and may employ a fluid-dispenser driver that uses interchangeable cassettes. These cassettes may contain assay fluids within a number of reservoirs, and may be controlled so that they deposit the assay fluids into the wells of the well plate. The well plate including a reaction medium may be moved relative to the cassette so that an assay fluid may be ejected by a number of fluid ejection dies at different wells of the well plate. The well plate may be, for example, a microliter plate in which an array of reaction wells is defined. Further, in one example, the assay fluid dispensing system may dispense the at least one assay fluid onto a tissue sample, a chip with integrated microfluidics, or a glass slide.

Multi-channel cassettes may be used so that multiple fluids may be dispensed contemporaneously. For example, multiple samples may be deposited within respective wells of the well plate in parallel or in serial in order to reduce the time in titrating a plurality of samples within the wells. As used in the present specification and in the appended claims, the term "cassette" is meant to be understood broadly as any user-replaceable component of an assay fluid dispenser system, through which at least one fluid flow through at least one fluid channel before being dispensed from the assay fluid dispensing system.

One example of a multi-channel fluid-dispenser cassette may be, for example, a T-8 cassette for use with the HP® D300 Digital Dispenser. In this example, the channels are nominally identical, as is appropriate, for example, when titrating a set of samples with similar fluid properties. However, many assay protocols may call for the use of different assay fluids with very different fluid properties or handling protocols. For example, some assay fluids are more viscous than others. Further, some assay fluids may be dispensed in large volumes in order to take effect. Still other assay fluids such as, for example, potent samples, may be dispensed in small, precisely controlled amounts in order to take effect. In still another example, some assay fluids may be dispensed at specific conditions such as in the presence of conduit coatings and temperature controls to take effect.

Moreover, many assay protocols may stipulate the exact sequence and timing of the fluid handling and other non-dispensing steps, such as mixing or reading.

Thus, a number of cassettes may be used within the assay fluid dispenser system to achieve a wide variety of different reactions. In allowing a user to replace the cassettes may result in user error in properly aligning a number of electrical contacts on the interchangeable cassettes with a number of electrical contacts of the fluid-dispenser driver. Further, allowing a user to replace the cassettes may result in damage to the electrical contacts on the interchangeable cassettes such that the integrity of the cassettes may be compromised.

Examples described herein provide a cassette. The cassette may include a substrate, a die coupled to the substrate, and an electrical interconnection pad layout formed on a first side of the substrate. The electrical interconnection pad layout may include a first row of interconnect pads including at least one interconnect pad. Each interconnect pad of the first row of interconnect pads may be electrically coupled to one of a first set of vias. The electrical interconnection pad layout may also include a second row of interconnection pads including at least one interconnect pad. Each interconnect pad of the second row of interconnect pads being electrically coupled to one of a second set of vias. The second set of vias electrically coupled to the second row of interconnect pads are offset relative to an alignment of the interconnect pads of the first and second rows.

In the examples herein, the cassette may further include a number of electrical traces formed on a second side of the substrate. The first and second sets of vias electrically couple the electrical interconnection pad layout to the electrical traces. The offset of the second set of vias electrically coupled to the second row of interconnect pads creates an offset of the electrical traces formed on a second side of the substrate. Further, in the examples herein, at least one of the interconnect pads of the first row of interconnect pads may include a contact seat defined therein. The contact seat allows for the seating of a pogo connection. Further, in the examples herein, at least one of the interconnect pads of the second row of interconnect pads may include a fire interconnect pad.

Examples described herein further provide a system for ejecting a fluid into an assay. The system may include a printed circuit assembly (PCA). The PCA may include at least one pogo connector, and at least one dispense head. The at least one dispense head may include a substrate, a die coupled to the substrate, and an electrical interconnection pad layout formed on a first side of the substrate. The electrical interconnection pad layout may include a first row of interconnect pads including at least one interconnect pad. Each interconnect pad of the first row of interconnect pads may be electrically coupled to one of a first set of vias. The electrical interconnection pad layout may include a second row of interconnect pads comprising at least one interconnect pad. Each interconnect pad of the second row of interconnect pads may be electrically coupled to one of a second set of vias. The second set of vies electrically coupled to the second row of interconnect pads are offset relative to an alignment of the interconnect pads of the first and second rows.

In the examples herein, at least one of the interconnect pads of the second row of interconnect pads may include a fire interconnect pad. Further, in one example, at least one of the interconnect pads of the first row of interconnect pads may include a contact seat defined therein. The contact seat allows for the seating of at least one of the pogo connectors therein when the at least one dispense head interfaces with the PCA.

In the examples herein, the first row of interconnect pads may include at least a ground interconnect pad, a source voltage interconnect pad, and a thermal sense resistor (TSR) interconnect pad. Further, in one example, the second row of interconnect pads may include at least a fire interconnect pad, a clock interconnect pad, and a data interconnect pad. The PCA interfaces with the electrical interconnection pad layout of the at least one dispense head by sliding the at least one pogo connector over the second row of interconnect pads and electrically coupling the at least one pogo connector to at least one interconnect pad of the first row of interconnect pads. The PCA interfaces with the electrical interconnection pad layout of the at least one dispense head by dropping the at least one pogo connector onto at least one interconnect pad in the first or second rows of interconnect pads in a direction perpendicular to a plane formed by the electrical interconnection pad layout.

Examples described herein further provide a method of forming a cassette. The method may include forming a monolithic substrate. An electrical interconnection pad layout may be formed on a first side of the monolithic substrate. The electrical interconnection pad layout may be formed (block 1302) by forming a first row of interconnect pads including at least one interconnect pad, where each interconnect pad of the first row of interconnect pads being electrically coupled to one of a first set of vias. Further, the electrical interconnection pad layout may be formed by forming a second row of interconnection pads including at least one interconnect pad, where each interconnect pad of the second row of interconnect pads is electrically coupled to one of a second set of vias. Further, the electrical interconnection pad layout may be formed by offsetting the second set of vias electrically coupling to the second row of interconnect pads relative to an alignment of the interconnect pads of the first and second rows.

In the examples herein, the method may further include forming at least one contact seat into at least one interconnect pad of the first row of interconnect pads. Further, the method may further include defining a number of electrical traces on a second side of the monolithic substrate electrically coupling a die to the first and second sets of vias. In one example, the number of electrical traces may be defined using a laser direct structuring (LDS) process.

As used in the present specification and in the appended claims; the term "a number of" or similar language is meant to be understood broadly as any positive number comprising 1 to infinity; zero not being a number, but the absence of a number.

In the following description, for purposes of explanation; numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may or may not be included in other examples.

Figure 2:
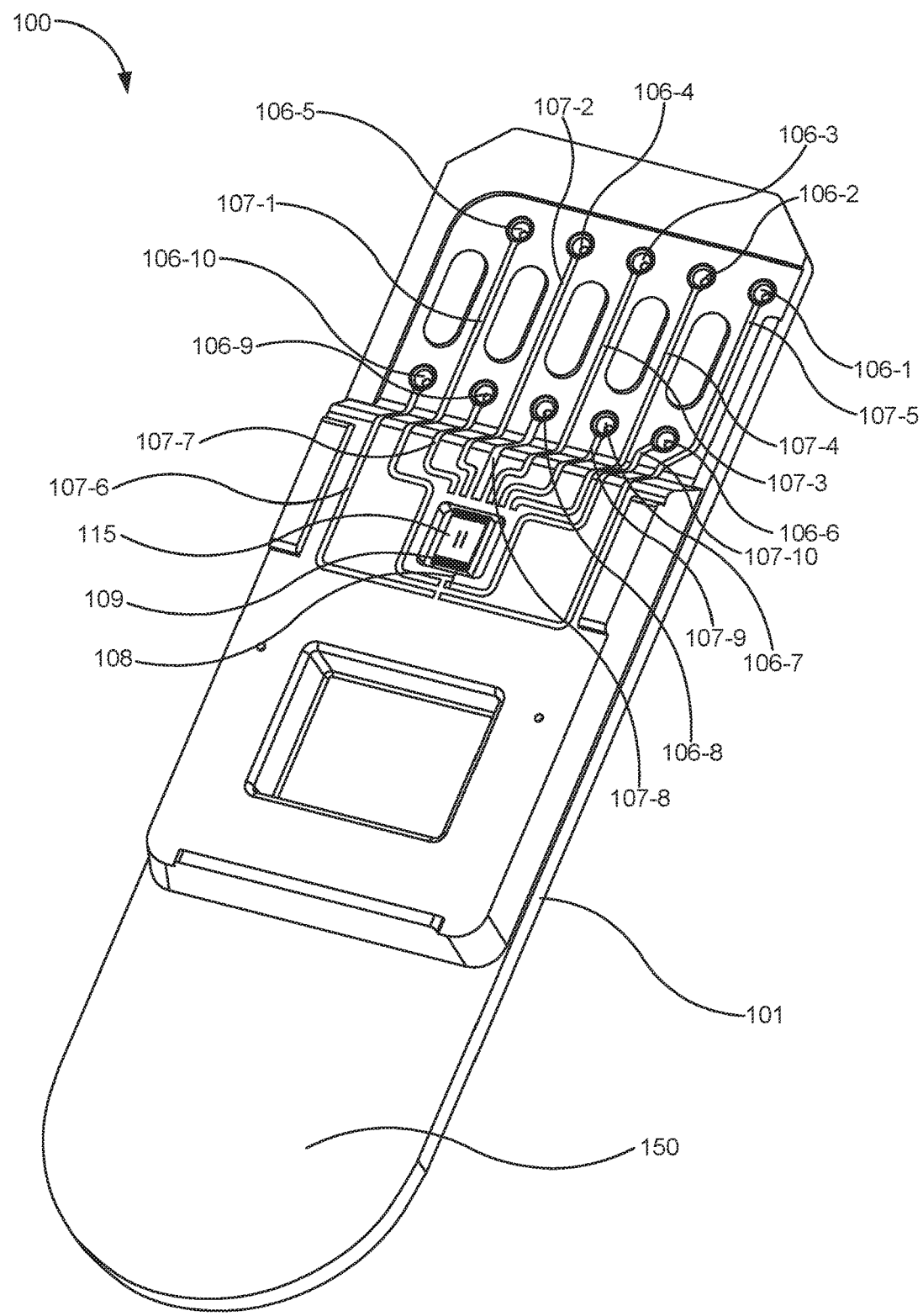
FIG. 2 is a back, perspective view of the first volume cassette of FIG. 1, according to one example of the principles described herein.

Turning now to the figures; FIG. 1 is a front, perspective view of a first volume cassette (100), according to one example of the principles described herein. Further, FIG. 2 is a back, perspective view of the first volume cassette (100) of FIG. 1, according to one example of the principles described herein. The first volume cassette (100) may include a substrate (101). In one example, the substrate (101) may be made of a thermoplastic material. A reservoir (102) with a fluid aperture (103) defined in the reservoir (102). The fluid aperture (103) allows for an assay fluid to move from one side of the substrate (101) to another. The substrate (101) may include a handle (150) to allow a user to touch, pick up, and move the cassette (100) without contaminating the reservoir (102) or an assay fluid deposited therein.

A die (104) may be coupled to the substrate (101) on an opposite side of the reservoir (102) and in line with the fluid aperture (103). In one example, the die (104) may be, for example, a microelectromechanical system (MEMs). In another example, the die may be a fluid ejection device.

The reservoir (101) is fluidically coupled to the die (104) by the fluid aperture (103) so that the assay fluid may be introduced to the die (104) to allow the die (104) to eject the assay fluid into a number of the wells of the well plate as instructed by an assay fluid dispensing system.

A number of electrical components are included on the front and back surfaces of the substrate (101). The electrical components may be made of any electrically conductive material to allow for electrical signals to be sent between the assay fluid dispensing system and the die (104). For example, a number of contact pads (105-1, 105-2, 105-3, 105-4, 105-5, 105-6, 105-7, 105-8, 105-9, 105-10, collectively referred to herein as 105) may be included on the front surface of the substrate (101). The contact pads (105) provide for an electrically conducive interface between the assay fluid dispensing system and the cassette (100).

A number of vias (106-1, 106-2, 106-3, 106-4, 106-5, 106-6, 106-7, 106-8, 106-9, 106-10, collectively referred to herein as 106) may be formed in the substrate (101) and electrically coupled to the contact pads (105). The vias (106) may be any electrical connection that goes through the substrate (101) and couples the connection pads (105) to a number of electrical components on the opposite side of the substrate (101).

A depicted in FIG. 2, the vias (106) are coupled on the opposite side of the substrate (101) to a number of traces (107-1, 107-2, 107-3, 107-4, 107-5, 107-6, 107-7, 107-8, 107-9, 107-10, collectively referred to herein as 107). The traces (107) may be coupled to the die (104) using a number of wirebonds (108) coupled between a number of die pads (109) of the die (104). Although one wirebond (108) coupled between a trace (107) and a die pad (109) is depicted in the figures, any number of wirebonds (108) may be used to electrically couple the die (104) to an assay fluid dispensing system to allow control signals for controlling the die (104) to run from the assay fluid dispensing system, through the contact pads (105), the vias (106), the traces (107), and the wirebonds (108), to the die pads (109) of the die (104).

Figure 3:
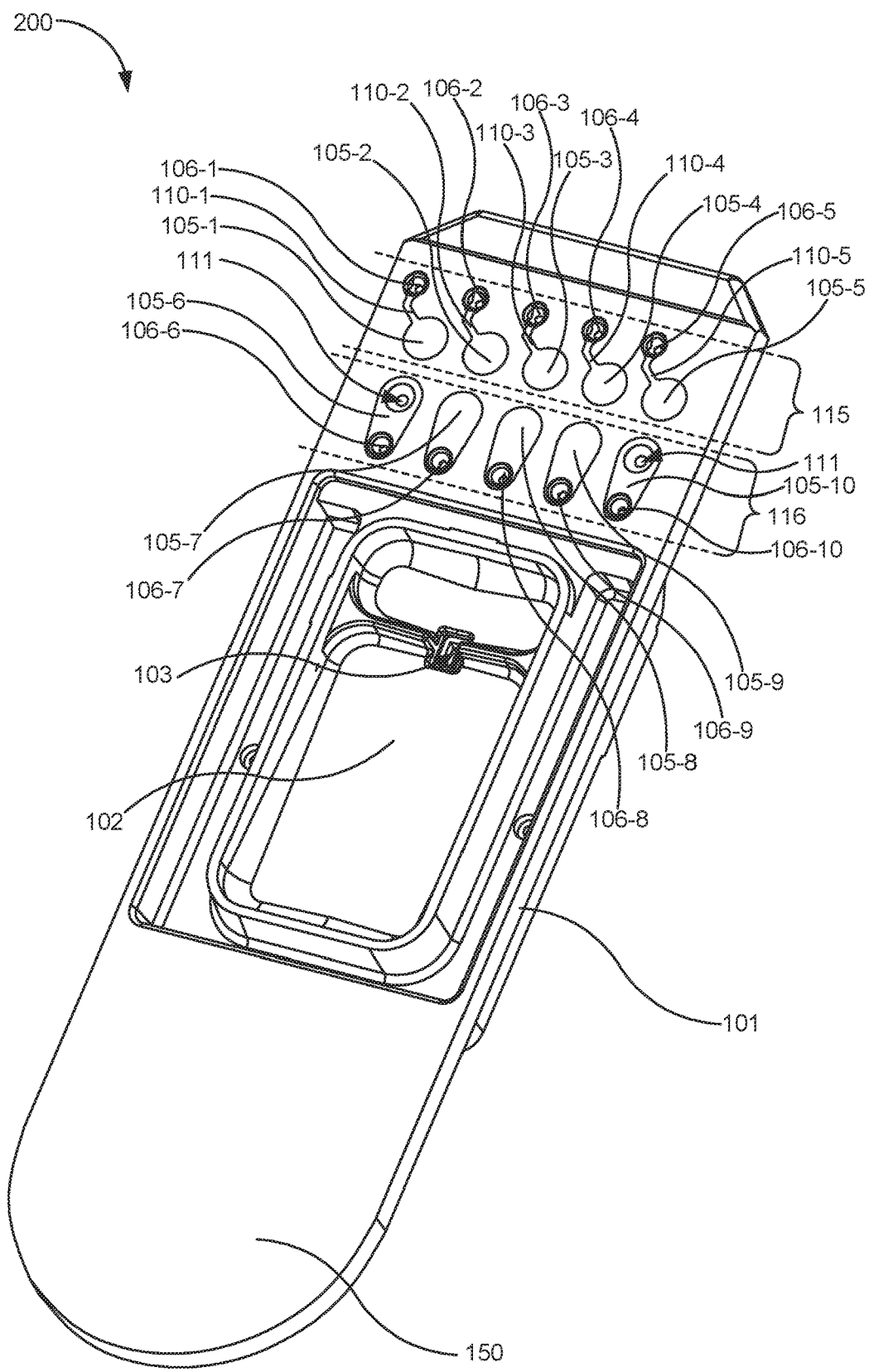
FIG. 3 is a front, perspective view of a second volume cassette, according to one example of the principles described herein.
Figure 4:
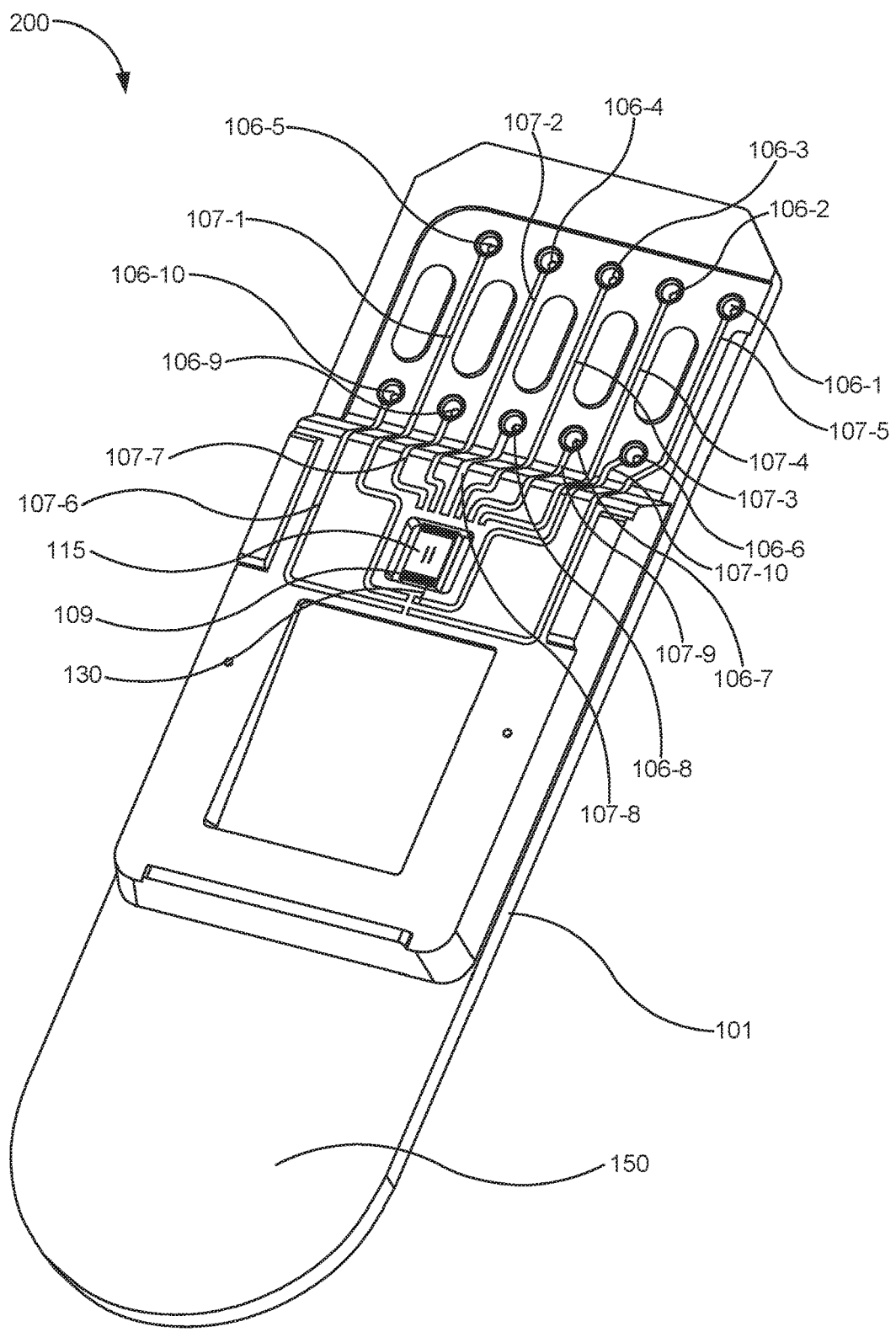
FIG. 4 is a back, perspective view of the second volume cassette of FIG. 3, according to one example of the principles described herein.

FIG. 3 is a front, perspective view of a second volume cassette (200), according to one example of the principles described herein. Further, FIG. 4 is a back, perspective view of the second volume cassette (200) of FIG. 3, according to one example of the principles described herein. The second volume cassette (200) includes elements identical to the first volume cassette (100) except for the volume of fluid that may be introduced into the reservoir (102). The reservoir (102) in the example of FIGS. 1 and 2, may be relatively smaller than the reservoir (102) in the example of FIGS. 3 and 4. In one example, the reservoir (102) of FIGS. 1 and 2 may be sized to contain approximately 20 microliters of fluid, while the reservoir (102) of FIGS. 3 and 4 may be sized to contain a fluid volume greater than 20 microliters.

In one example, the electrical components of the examples of the first volume cassette (100) and the second volume cassette (200) including the contact pads (105), the vias (106), the traces (107), and the wirebonds (108) may be formed using a laser direct structuring (LDS) process. An LDS process uses a thermoplastic material, doped with a non-conductive, metallic, inorganic compound activated by a laser. In this example, the substrate (101) may be formed through injection molding. A laser may then write the course of a number of electrical components to be formed on the thermoplastic material. Where the substrate (101) is exposed to the electromagnetic radiation provided by laser, the metal additive forms a micro-rough track. The metal particles of this track form the nuclei for a subsequent metallization process. The laser-exposed substrate (101) may be placed in an electroless copper bath, and the various conductor path layers of the electrical components arise at those portions of the substrate (101) exposed to the electromagnetic radiation of the laser. Any number of successive layers of metals such as copper, nickel and gold may be deposited on the portions of the substrate (101) exposed to the electromagnetic radiation of the laser. LDS processes allow for the precise, computer-aided formation of the electrical components on the surfaces of the substrate (101).

In another example, the electrical components of the examples of the first volume cassette (100) and the second volume cassette (200) including the contact pads (105), the vias (106), the traces (107), and the wirebonds (108) may be formed may be formed using a deposition process where a conductive material is deposited on the substrate (101). In this example, the conductive material may be deposited using, for example, a three-dimensional (3D) printing device.

With reference now to the examples of FIGS. 1 through 4 of the first volume cassette (100) and the second volume cassette (200), the contact pads (105) may be laid out on the front surface of the substrate (101) in two rows (115, 116) with a first set of contact pads (105-1, 105-2, 105-3, 105-4, 105-5) being included in a first row (115) and a seconds set of contact pads (105-6, 105-7, 105-8, 105-9, 105-10) being included in a second row (116). This arrangement of the contact pads (105) allows for the cassette to be smaller in size while still providing for a large number of interfaces.

The vias (106) of FIGS. 1 through 4 may be arranged such that the vias (106-1, 106-2, 106-3, 106-4, 106-5) coupled to the first row (115) of contact pads (105-1, 105-2, 105-3, 105-4, 105-5) are located on an side of their respective contact pads (105-1, 105-2, 105-3, 105-4, 105-5) that is furthest away from the contact pads (105-6, 105-7, 105-8, 105-9, 105-10) included in the second row (116), and the vias (106-6, 106-7, 106-8, 106-9, 106-10) coupled to the second row (116) of contact pads (105-6, 105-7, 105-8, 105-9, 105-10) are located on an side of their respective contact pads (105-6, 105-7, 105-8, 105-9, 105-10) that is furthest away from the contact pads (105-1, 105-2, 105-3, 105-4, 105-5) included in the first row (115).

Figure 5:
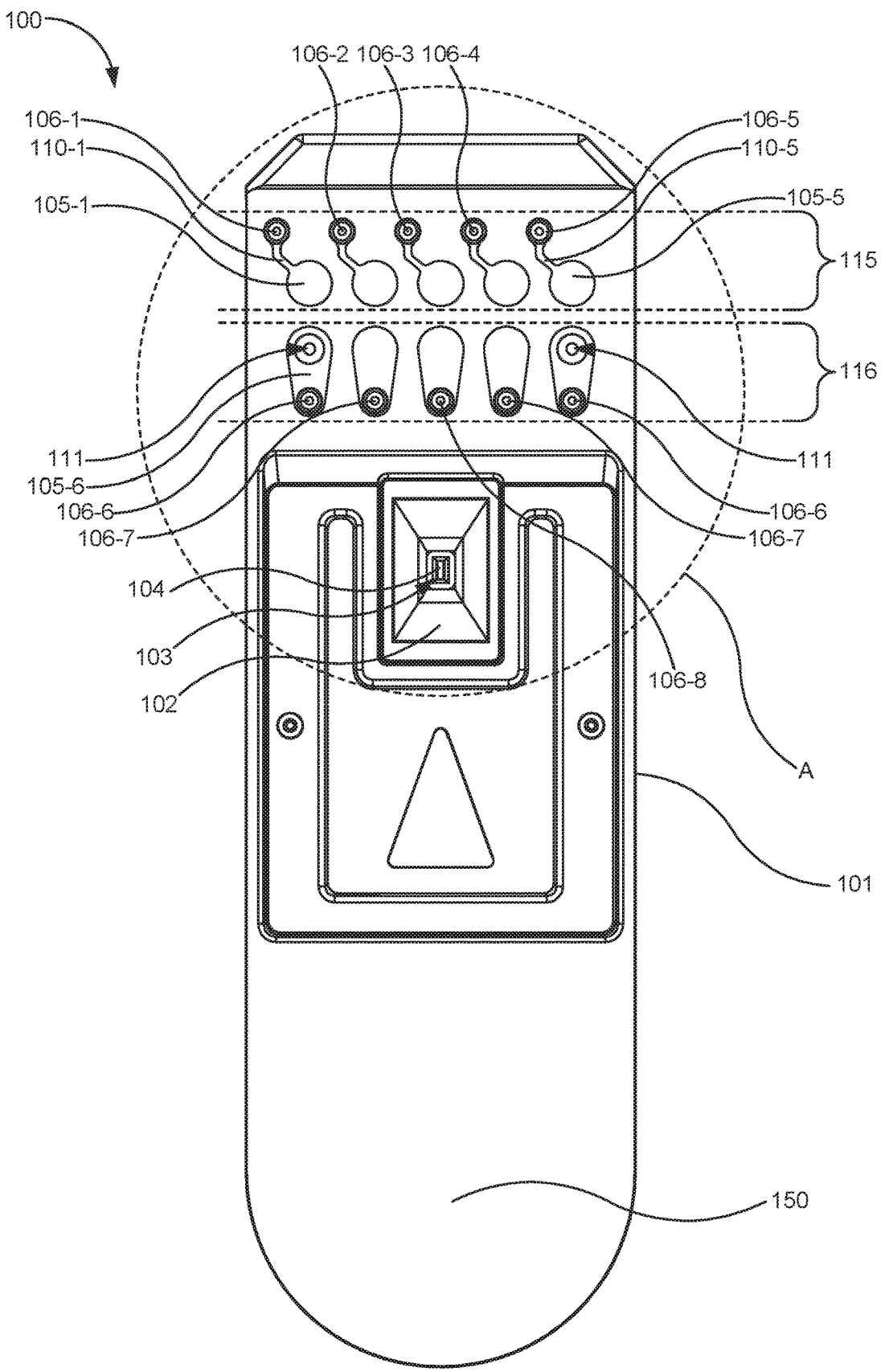
FIG. 5 is a front, plan view of the first volume cassette of FIG. 1, according to one example of the principles described herein.
Figure 6:
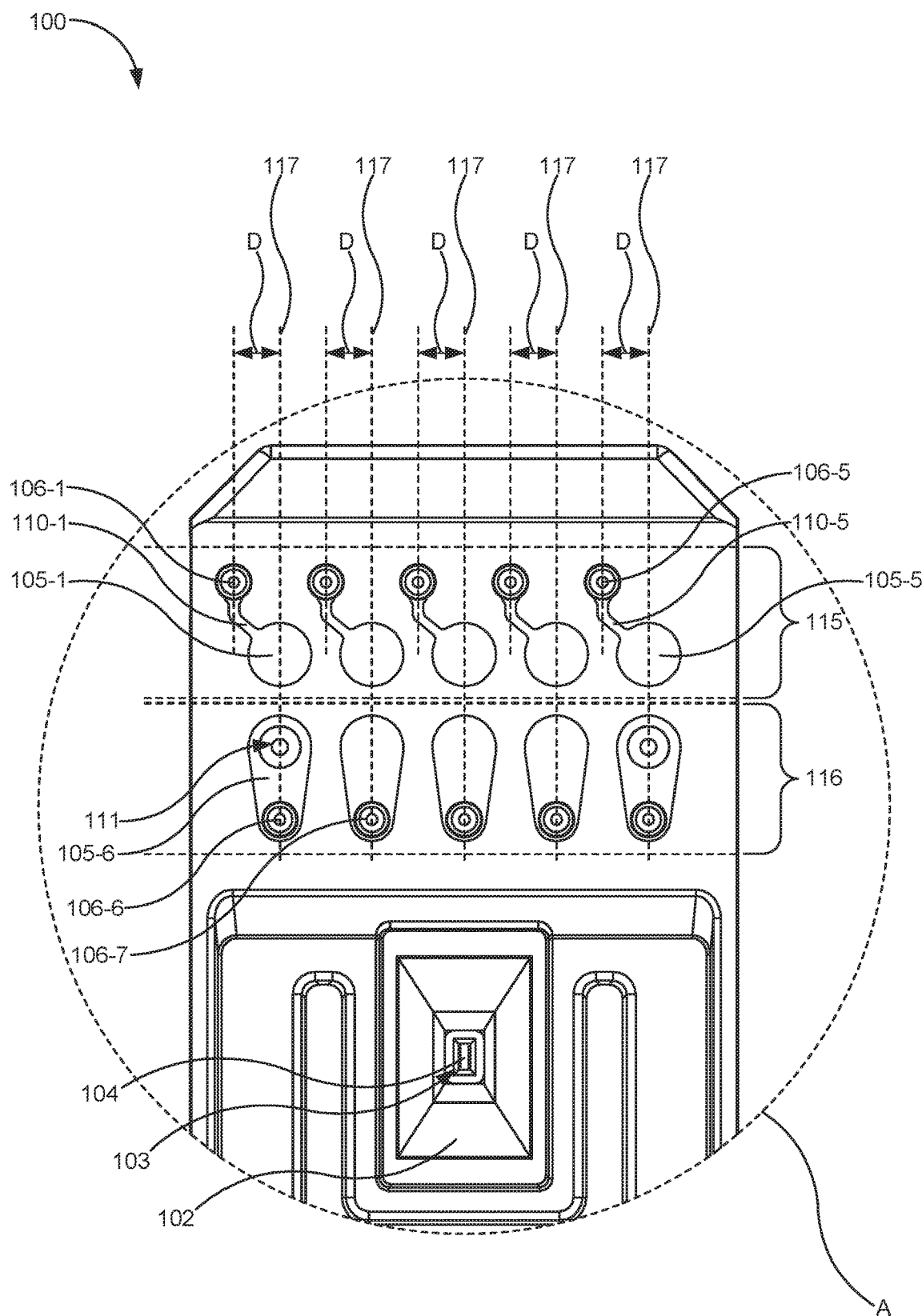
FIG. 6 is a front, plan view of the first volume cassette of FIG. 1 as viewed in circle A of FIG. 5, according to one example of the principles described herein.
Figure 7:
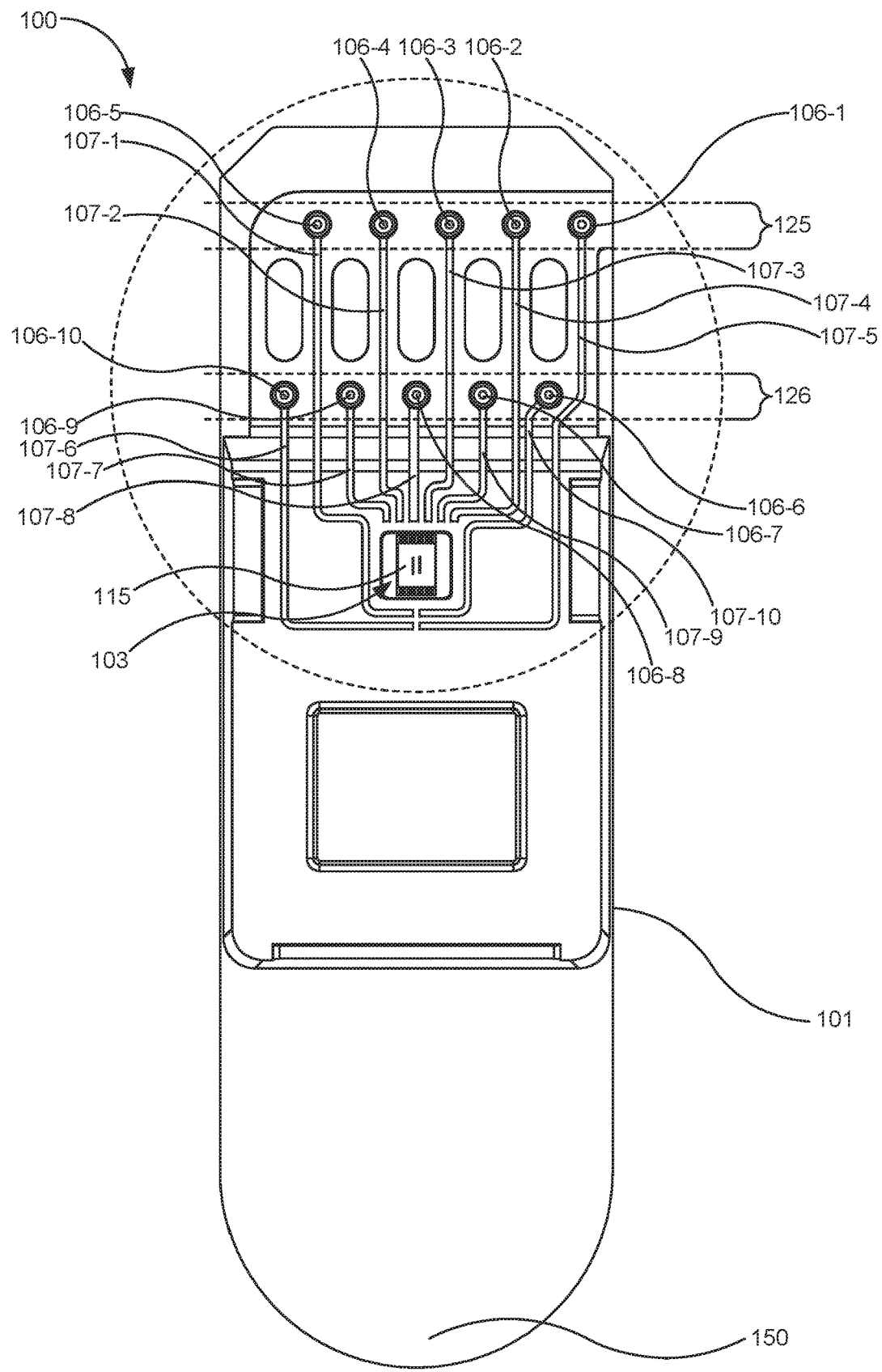
FIG. 7 is a back, plan view of the first volume cassette of FIG. 1, according to one example of the principles described herein.
Figure 8:
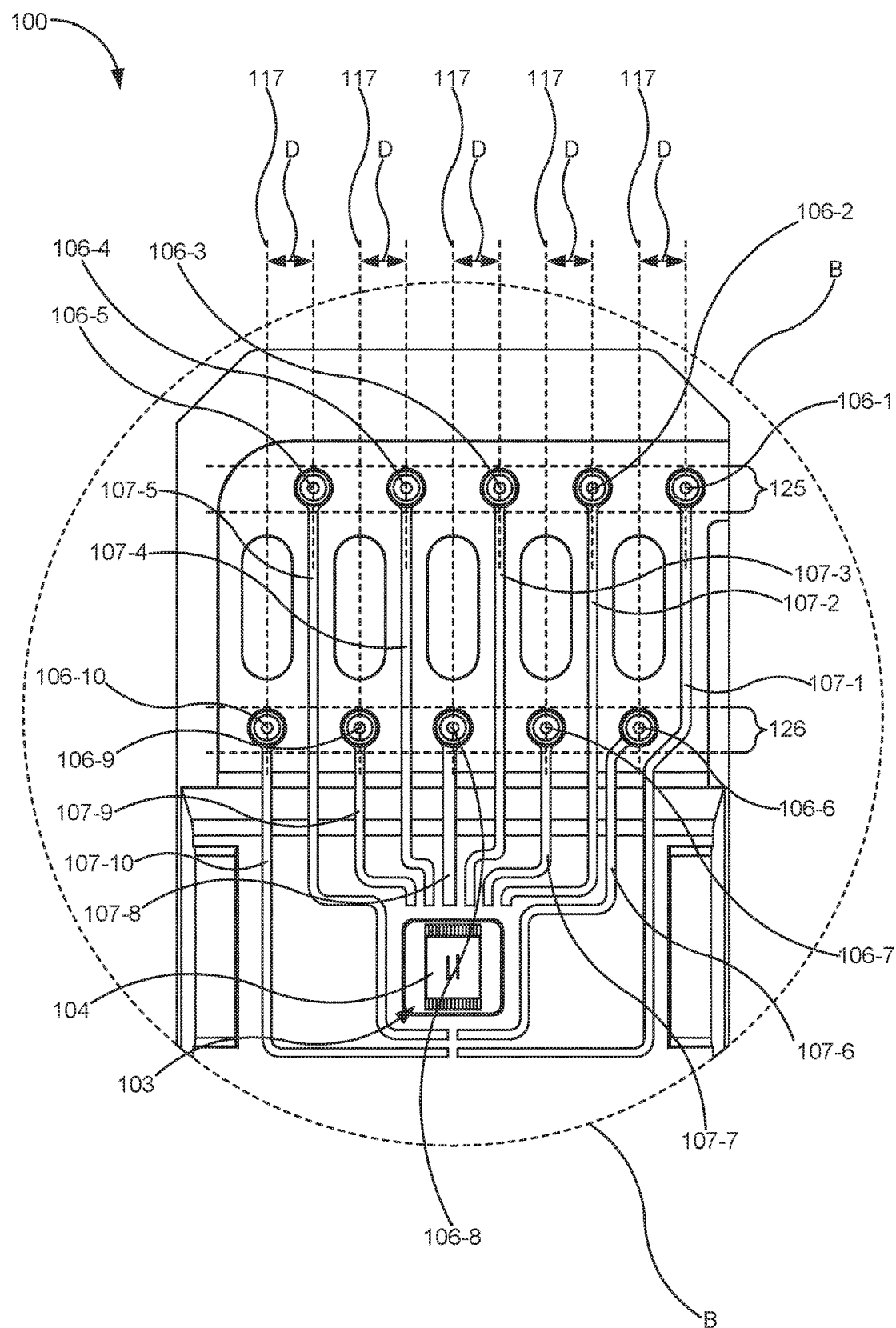
FIG. 8 is a back, plan view of the first volume cassette of FIG. 1 as viewed in circle B of FIG. 7, according to one example of the principles described herein.

Further, the vias (106-1, 106-2, 106-3, 106-4, 106-5) are coupled to the first row (115) of contact pads (105-1, 105-2, 105-3, 105-4, 105-5) using a respective offsetting trace (110-1, 110-2, 110-3, 110-4, 110-5, collectively referred to herein as 110). The offsetting traces (110) of FIGS. 1 through 4 cause the vias (106-1, 106-2, 106-3, 106-4, 106-5) of the first row (115) of contact pads (105-1, 105-2, 105-3, 105-4, 105-5) to be laterally offset with respect to the vias (106-6, 106-7, 106-8, 106-9, 106-10) of the second row (116) of contact pads (105-6, 105-7, 105-8, 105-9, 105-10). This offset layout is depicted in FIGS. 5-8. FIG. 5 is a front, plan view of the first volume cassette (100) of FIG. 1, according to one example of the principles described herein. Further, FIG. 6, is a front, plan view of the first volume cassette (100) of FIG. 1 as viewed in circle A of FIG. 5, according to one example of the principles described herein. Still further, FIG. 7 is a back, plan view of the first volume cassette (100) of FIG. 1, according to one example of the principles described herein. Still further, FIG. 8 is a back, plan view of the first volume cassette (100) of FIG. 1 as viewed in circle B of FIG. 7, according to one example of the principles described herein. Even though the first volume cassette (100) is used in describing the offset layout of the vias (106), the second volume cassette (200) and its electrical component layout may be described in an identical manner. For convenience in understanding the offset layout of the vias (106) in the rows (115, 116), some reference numbers have been omitted. However, the reader may readily identify the various elements within the cassettes (100, 200) through reference to other figures including FIGS. 1 through 4.

As depicted in FIGS. 5 and 6, the vias (106-1, 106-2, 106-3, 106-4, 106-5) are coupled to the first row (115) of contact pads (105-1, 105-2, 105-3, 105-4, 105-5) using a respective offsetting trace (110-1, 110-2, 110-3, 110-4, 110-5, collectively referred to herein as 110). The offsetting traces (110) of FIGS. 1 through 4 cause the vias (106-1, 106-2, 106-3, 106-4, 106-5) of the first row (115) of contact pads (105-1, 105-2, 105-3, 105-4, 105-5) to be laterally offset with respect to the vias (106-6, 106-7, 106-8, 106-9, 106-10) of the second row (116) of contact pads (105-6, 105-7, 105-8, 105-9, 105-10). As depicted in circle A of FIGS. 4 and 5, the offset traces (110) are angled with respect to the alignment of the contact pads (105) and the vias (106-6, 106-7, 106-8, 106-9, 106-10) of the second row (116) as indicated by lines 117. Thus, the offset may be defined by distance D from lines 117. More regarding the distance D and its function is described herein.

Further, with respect to FIGS. 1 through 8, and specifically FIGS. 7 and 8, because the vias (106-1, 106-2, 106-3, 106-4, 106-5) coupled to the first row (115) of contact pads (105-1, 105-2, 105-3, 105-4, 105-5) using their respective offsetting traces (110), a similar offset layout is reflected on an opposite side of the substrate (100) in the layout of the traces (107). Each via (106) in a first row (125) of vias (106-1, 106-2, 106-3, 106-4, 106-5) is offset with respect to each via (106) in a second row (126) of vias (106-6, 106-7, 106-8, 106-9, 106-10). Further, due to the offsetting of the vias (106), their respective traces (107) are also offset. In this manner, the layout of the contact pads (105), vias (106), and traces (107) allows for space on the substrate (101) for all these devices.

Figure 9:
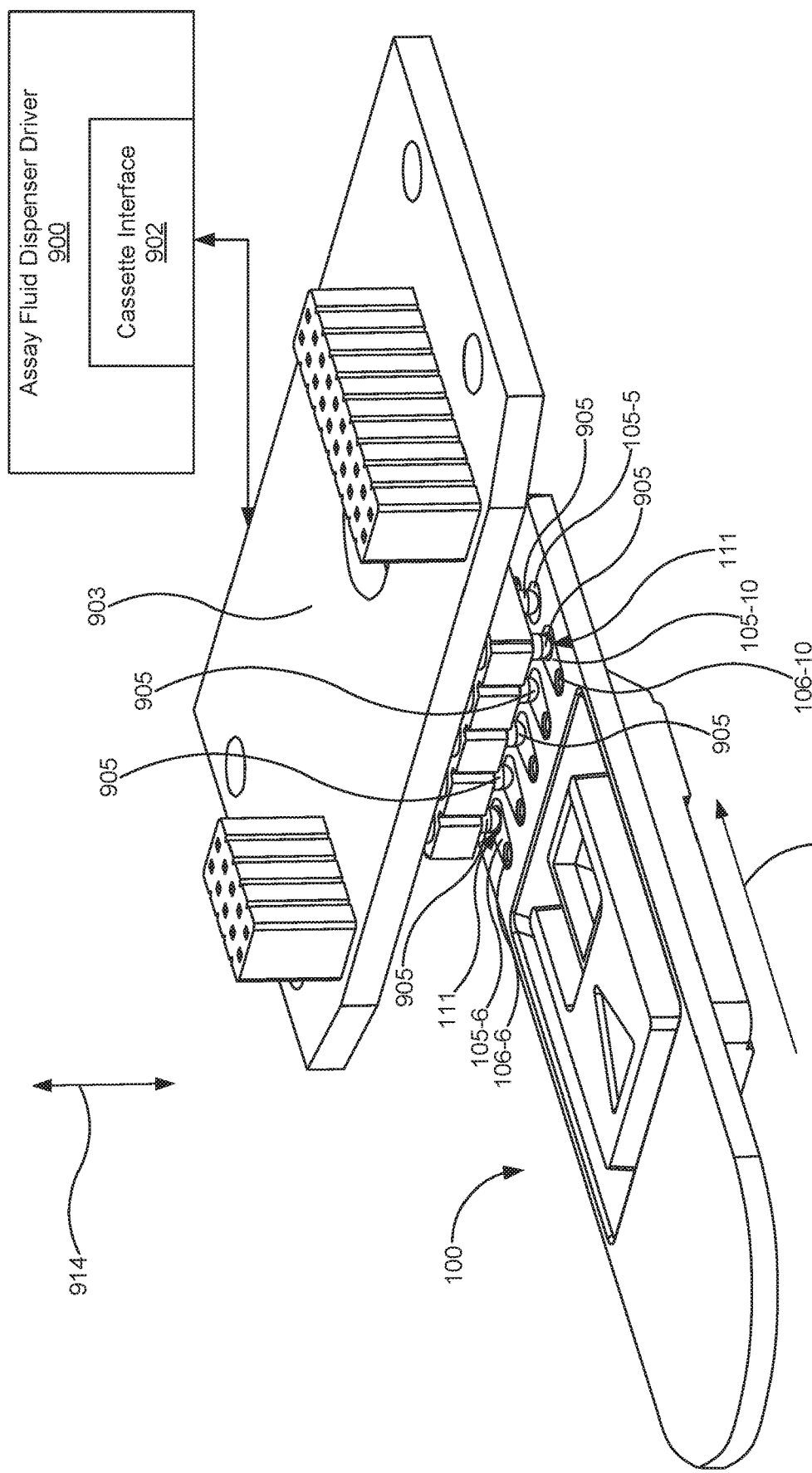
FIG. 9 is a perspective view of the first volume cassette of FIG. 1 interfaced with a printed circuit assembly (PCA) of a cassette interface of an assay fluid dispenser driver, according to one example of the principles described herein.

FIG. 9 is a perspective view of the first volume cassette (100) of FIG. 1 interfaced with a printed circuit assembly (PCA) (903) of a cassette interface (901) of an assay fluid dispenser driver (900), according to one example of the principles described herein. Although the first volume cassette (100) is depicted in FIG. 9, the cassette (200) of FIGS. 3 and 4 may also function and be utilized in a similar manner. In one example, the cassette (100, 200) may interface with the PCA (903), a cassette interface (902), and the assay fluid dispenser driver (900) by inserting the cassette (100, 200) along a number of alignment surfaces or registers of the assay fluid dispenser driver (900) in the direction of arrow (904). In another example, the PCA (903) and/or the cassette (100, 200) may move in the directions indicated by arrow (914) to interface the cassette (100, 200) with the PCA (903). In this example, the cassette (100, 200) may be placed in a station of the assay fluid dispenser driver (900), and the assay fluid dispenser driver (900) moves the PCA (903) onto the cassette (100, 200) in the direction of arrow (914) until contact between the PCA (903) and the contact pads (105) of the cassette (100, 200) is achieved. In still another example, a combination of inserting a cassette (100, 200) along a number of alignment surfaces of the assay fluid dispenser driver (900) in the direction of arrow (904) and the movement PCA (903) and/or the cassette (100, 200) in the directions indicated by arrow (914) may be used to interface the cassette (100, 200) with the PCA (903).

The PCA (903) may include a number of pogo connectors (905) that electrically couple the contact pads (105) formed on the cassette (100, 200) to the PCA (903). The pogo connectors (905) may be any device used in electronics to establish a connection between the contact pads (105) formed on the cassette (100, 200) and the PCA (903), and may include two, nested, spring-loaded pins. In one example, the PCA (903) may include an equal number of pogo connectors (905) as there are contact pads (105) formed on the cassette (100, 200). In another example, the PCA (903) may include more or fewer pogo connectors (905) as there are contact pads (105) formed on the cassette (100, 200). In these examples, the pogo connectors (905) may be arranged on the PCA (903) such that they align with the contact pads (105) when the cassette (100, 200) is interfaced with the PCA (903).

In one example, a number of detents or contact seats (FIGS. 1, 3, 5, 6, and 9, 111) may be defined in a surface of the contact pads (105). These detents (111) interface with the pogo connectors (905) as the cassette (100, 200) is interfaced with the PCA (903). One the pogo connectors (905) enter the detents (111), the cassette (100, 200) is removably coupled to the PCA (903). Removal of the cassette (100, 200) may be performed by overcoming the pressure applied to the cassette (100, 200) by the spring-loaded pogo connectors (905), causing the pogo connectors (905) to contract and moving the pogo connectors (905) out of the detents (111).

Turning again to FIGS. 5 and 6, along with FIG. 9, in one example where the cassette (100, 200) is interfaced with the PCA (903) by inserting the cassette (100, 200) along a number of alignment surfaces of the assay fluid dispenser driver (900) in the direction of arrow (904), the pogo connectors (905) are dragged across the top of the substrate (101) and across the contact pads (105). This at least partially due to the spring bias of the pogo connectors (905). As the cassette (100, 200) is inserted into a coupling arrangement with the PCA (903), the frictional force applied by the pogo connectors (905) being dragged across the top of the substrate (101) may damage electrical connections formed on the cassette (100, 200). The drag path of the pogo connectors (905) is identified by lines (117) of FIG. 6. Dragging the pogo connectors (905) across electrical elements such as vias (106) and traces (107) may compromise the electrical connectivity integrity of these elements due to any damage the friction from the pogo connectors (905) may cause. Thus, the offset traces (110) formed on the cassette (100, 200) and electrically coupled to the contact pads (105-1, 105-2, 105-3, 105-4, 105-5) on the first row (115) eliminate the possibility that the pogo connectors (905) may damage, for example, vias (106-1, 106-2, 106-3, 106-4, 106-5) that may otherwise be placed in line with lines (117). If, for example, the vias (106) were formed in line with lines (117), the pogo connectors (905) would be dragged across those vias (106-1, 106-2, 106-3, 106-4, 106-5) during the insertion of the cassette (100, 200), and this friction-causing movement may damage the vias (106-1, 106-2, 106-3, 106-4, 106-5). In this manner, the offset traces (110) eliminate the possibility that the pogo connectors (905) may damage the vias (106-1, 106-2, 106-3, 106-4, 106-5).

Further, the offset traces (110) run diagonally from the contact pads (105-1, 105-2, 105-3, 105-4, 105-5) of the first row (115) to the vias (106-1, 106-2, 106-3, 106-4, 106-5) such that they too are not in line with the lines (117) along which the pogo connectors (905) travel. In this manner, the diagonal layout of the offset traces (110) eliminate damage to the thin offset traces (110).

As depicted throughout the figures, the vias (106-6, 106-7, 106-8, 106-9, 106-10) of the second row (116) coupled to the contact pads (105-6, 105-7, 105-8, 105-9, 105-10) are located at a position past the contact pads (105-6, 105-7, 105-8, 105-9, 105-10) and a distance of travel of the cassette (100, 200) within the assay fluid dispenser driver (900). In this position, the vias (106-6, 106-7, 106-8, 106-9, 106-10) will never be subjected to frictional contact by the pogo connectors (905) since they are beyond the reach of the travel distance of the pogo connectors (905) along the surface of the cassette (100, 200).

Further, each contact pad (105) may be logically assigned by, for example, the assay fluid dispenser driver (900) or some other controller such that each contact pad (105) is coupled through the contact pads (105), vias (106), traces (106), and wirebonds (108), to a respective one of the die pads (109) of the die (104). For example, the contact pad assignment may include the following:

TABLE 1

Contact Pad Assignment

| Contact Pad | Assignment |
|---|---|
| 105-1 | Ground and/or an Assignable |
| 105-2 | Data |
| 105-3 | Clock |
| 105-4 | Fire |
| 105-5 | Assignable |
| 105-6 | Assignable |
| 105-7 | $V_{DD}$ (source voltage) |
| 105-8 | Ground |
| 105-9 | Thermal Sense Resistor (TSR) |
| 105-10 | Ground and/or an Assignable |

The above contact pad assignment is an example, and other contact pad assignments may be made. In order to prevent or eliminate the possibility of damage to the electrical components of the assay fluid dispenser driver (900), the PCA (903), the cassette (100, 200), the die (104), any other electrical or electronic component, or combinations thereof, the contact pads assignments are arranged to ensure that a high voltage pogo connectors (905) is not dragged across any of the contact pads (105-1, 105-2, 105-3, 105-4, 105-5) in the first row (115). For example, the Fire contact pad (105-4) is located on the first row (115). In this location, the high voltage of the Fire contact pad (105-4) is coupled to the cassette (100, 200) as the last or one of the last contacts made between the cassette (100, 200) and the pogo connectors (905) of the PCA (903). Thus, the order of contact and assignment of the contact pads (105) is managed such that before, during, or after operation or powering of the PCA (903), no damage occurs to any electrical components of the cassette (100, 200), assay fluid dispenser driver (900), PCA (903), die (104), any other electrical or electronic component, or combinations thereof. Assignment of the contact pads (105) in this manner ensures that the assay process is performed without compromise to the assay run and the underlying reactions, and provides for a more economically reliable system.

Figure 10:
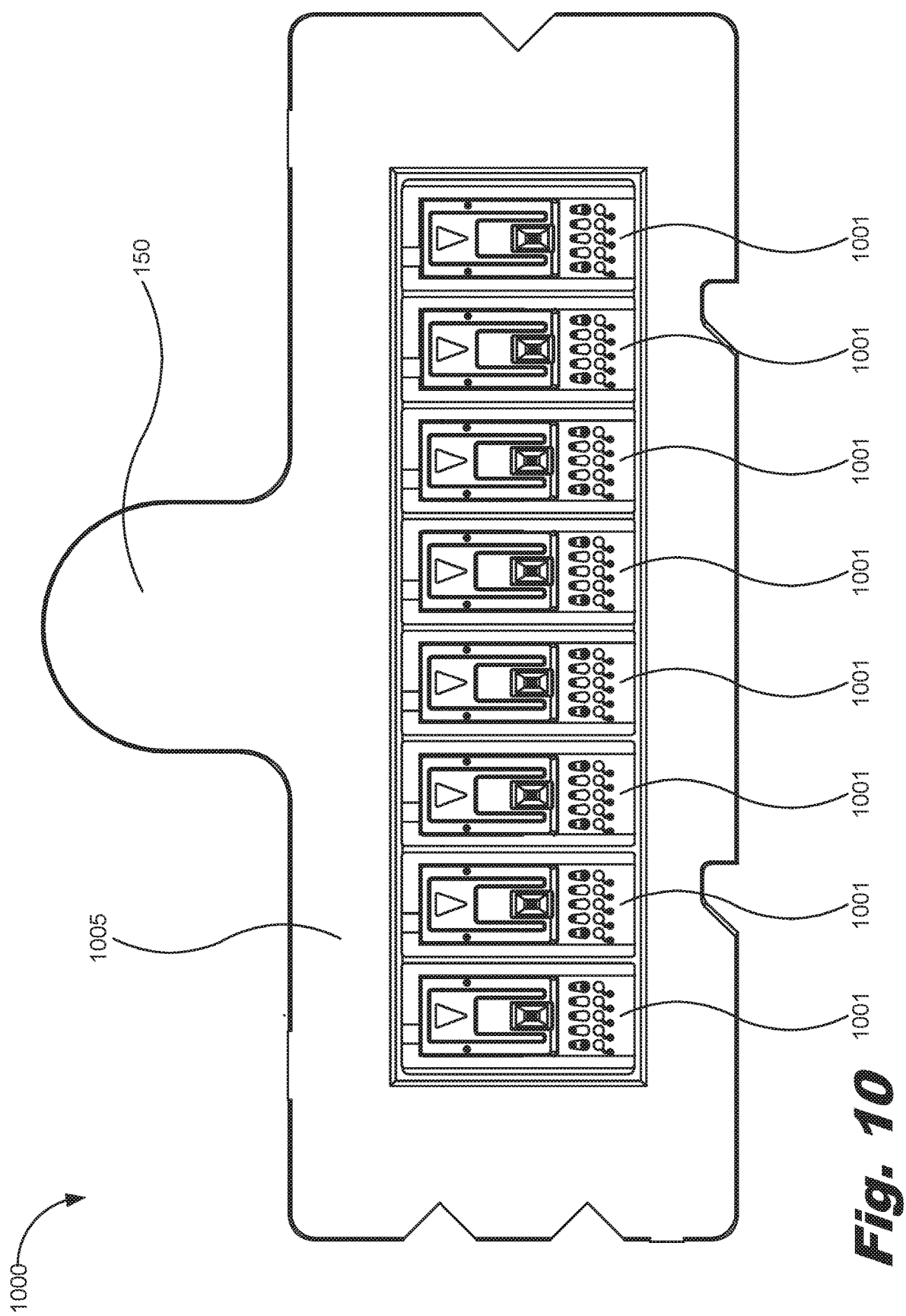
FIG. 10 is a front plan view of a cassette including a plurality of dispense head assemblies, according to one example of the principles described herein

FIG. 10 is a front plan view of a cassette (1000) including a plurality of dispense head assemblies (1001), according to one example of the principles described herein. Each of the dispense head assemblies (1001) may include the substrate (101), reservoir (102), fluid aperture (103), die (104), contact pads (105), vias (106), traces (107), wirebonds (108), die pads (109), offset traces (110), detents (111), and other elements as described above. In the example shown in FIG. 10, the dispense head assemblies (1001) are mounted onto a frame (1005). In an example, the dispense head assemblies (1001) may be mechanically coupled to the frame (1005) by, for example, a welding processes, a chemical bonding process, or by a number of fasteners. In an example, the frame (1005) forms the substrate (101) of each dispense head assemblies (1001) such that each of the dispense head assemblies (1001) are formed into a single monolithic frame (1005).

Figure 11:
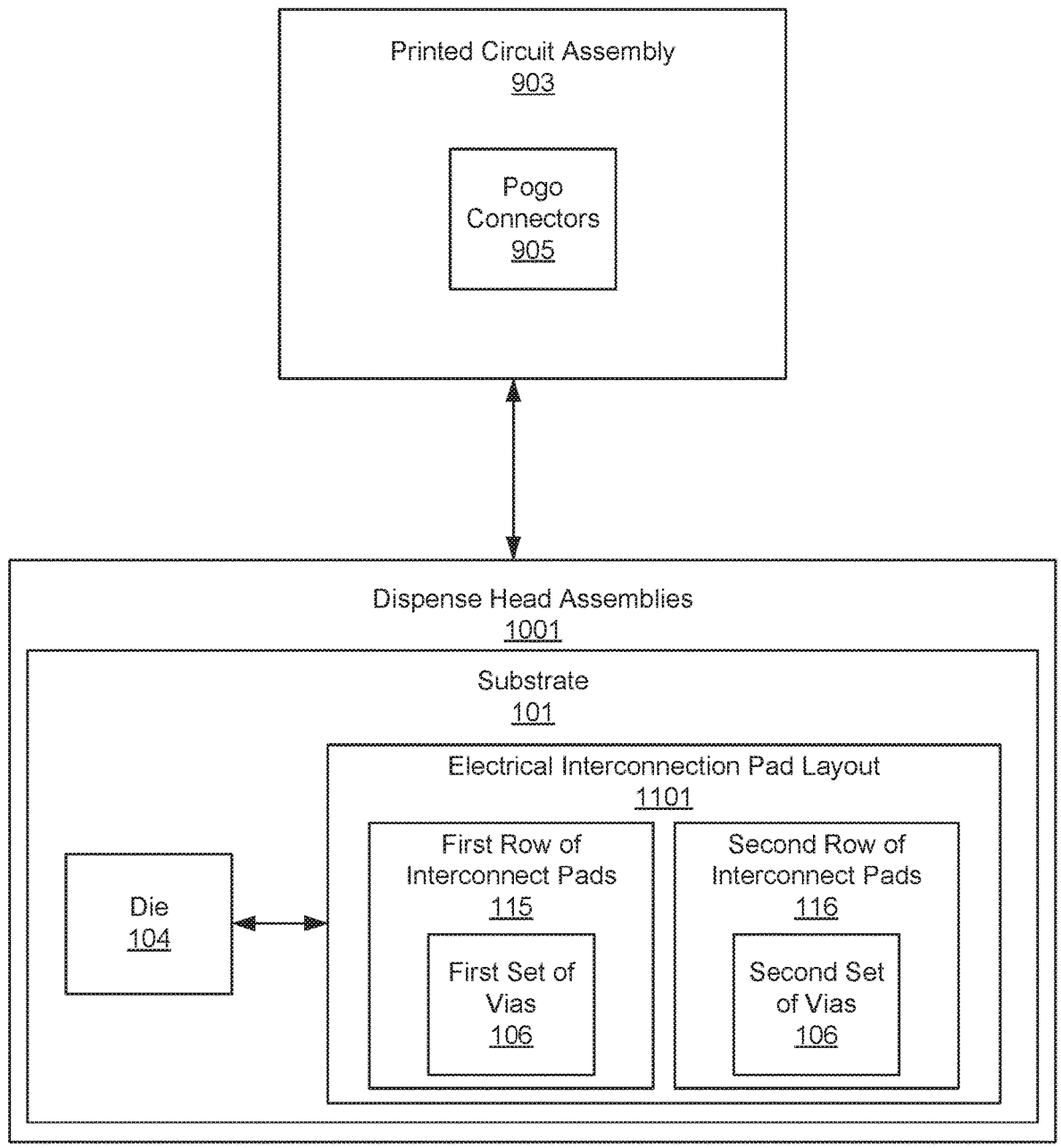
FIG. 11 is a block diagram of a system for ejecting a fluid into an assay, according to one example of the principles described herein.

FIG. 11 is a block diagram of a system (1100) for ejecting a fluid into an assay (1110), according to one example of the principles described herein. The system may include a printed circuit assembly (PCA) (9031). The PCA (903) may include at least one pogo connector (905), and at least one dispense head (1001). The at least one dispense head (1001) may include a substrate (101), a die (104) coupled to the substrate (101), and an electrical interconnection pad layout (1101) formed on a first side of the substrate (101). The electrical interconnection pad layout (1101) may include a first row (116) of interconnect pads (105) including at least one interconnect pad (105). Each interconnect pad (105) of the first row (116) of interconnect pads (105) may be electrically coupled to one of a first set (126) of vias (106). The electrical interconnection pad layout (1101) may include a second row (115) of interconnect pads (105) comprising at least one interconnect pad (105). Each interconnect pad (105) of the second row (115) of interconnect pads (105) may be electrically coupled to one of a second set (125) of vias (106). The second set (125) of vias (106) electrically coupled to the second row (115) of interconnect pads are offset relative to an alignment of the interconnect pads (105) of the first and second rows (115, 116).

In one example, at least one of the interconnect pads (105) of the second row (115) of interconnect pads (105) may include a fire interconnect pad. Further, in one example, at least one of the interconnect pads (105) of the first row (116) of interconnect pads (105) may include a contact seat (111) defined therein. The contact seat (111) allows for the seating of at least one of the pogo connectors (905) therein when the at least one dispense head (1001) interfaces with the PCA (903).

In one example, the first row (116) of interconnect pads (105) may include at least a ground interconnect pad, a source voltage interconnect pad, and a thermal sense resistor (TSR) interconnect pad. Further, in one example, the second row (115) of interconnect pads (105) may include at least a fire interconnect pad, a clock interconnect pad, and a data interconnect pad.

The PCA (903) interfaces with the electrical interconnection pad layout (1101) of the at least one dispense head (1001) by sliding the at least one pogo connector (905) over the second row (115) of interconnect pads (105) and electrically coupling the at least one pogo connector (105) to at least one interconnect pad (105) of the first row (116) of interconnect pads (105). The PCA (903) interfaces with the electrical interconnection pad layout (1101) of the at least one dispense head (1001) by dropping the at least one pogo connector (905) onto at least one interconnect pad (105) in the first or second rows (115, 116) of interconnect pads (105) in a direction perpendicular to a plane formed by the electrical interconnection pad layout (1101).

Figure 12:
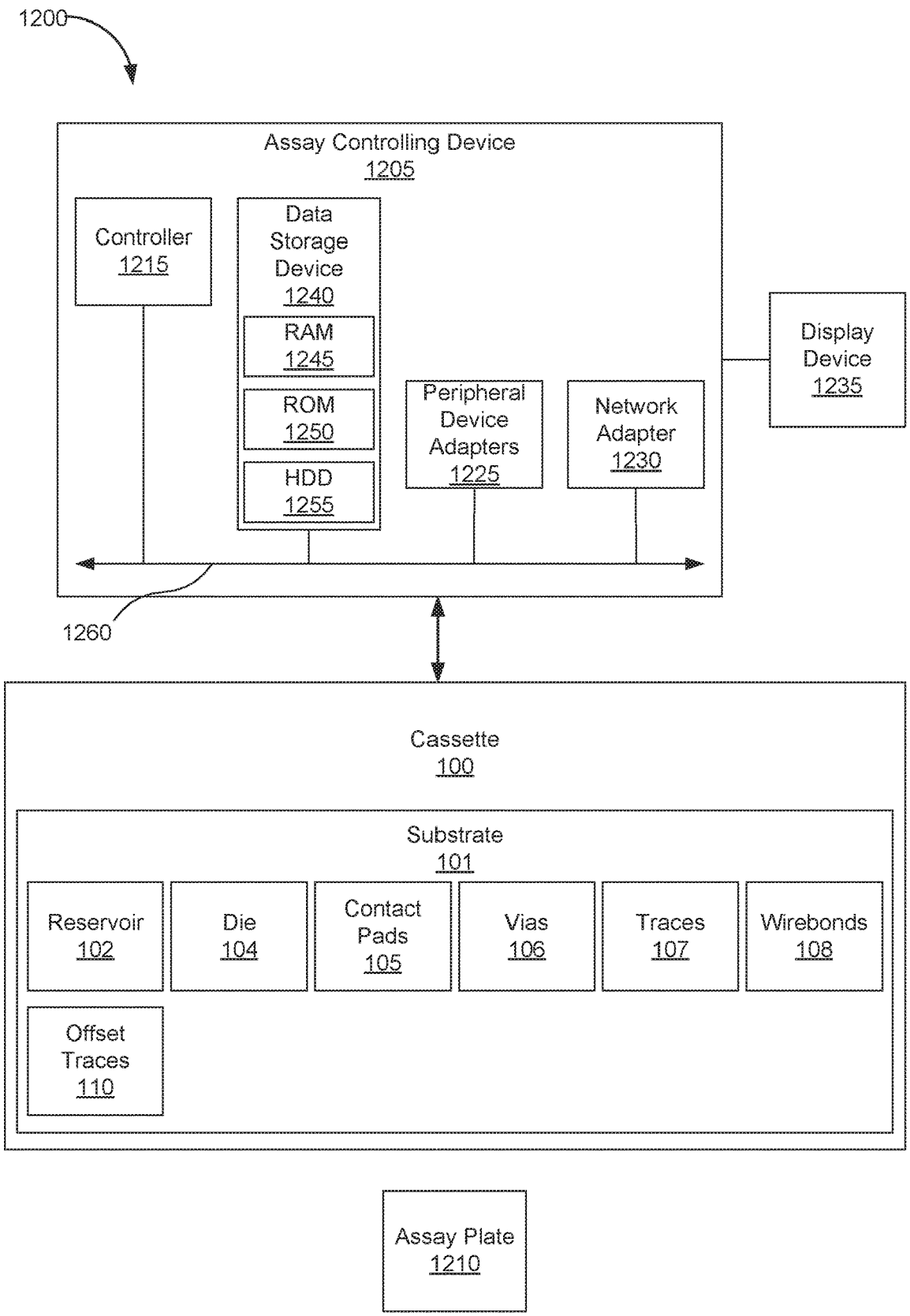
FIG. 12 is a block diagram of a system for ejecting a fluid into an assay, according to another example of the principles described herein.

FIG. 12 is a block diagram of a system (1200) for ejecting a fluid into an assay (1210), according to one example of the principles described herein. The system (1200) includes an assay controlling device (1205), a cassette (100, 200) as described above, and an assay plate (1210). Although the first volume cassette (100) is depicted in FIG. 11, either the second volume cassette (200), or combinations of the first volume cassette (100) and second volume cassette (200) with a frame (1005) may be included in the system (1200).

The cassette (100, 200) may include, at least, the substrate (101), reservoir (102), fluid aperture (103), die (104), contact pads (105), vias (106), traces (107), wirebonds (108), die pads (109), offset traces (120), and other elements as described above. Although the cassette (100, 200) shown in FIG. 12 does or does not include certain elements as described herein, each of the elements associated with the cassette (100, 200) may or may not be included. In order to achieve these different examples, the physical properties of the cassette (100, 200) may be changed. For example, where the cassette (100, 200) does not comprise the vias (106) as described above, the traces (107) and contact pads (105) may be included on a single side of the cassette (100, 200) such that the PCA (903) contacts the cassette (100, 200) via the back side of the cassette (100, 200) instead of the front.

The assay plate (1210) may be any plate that receives a fluid ejected from the die (104). The assay plate (1210) may include a number of wells into which the fluid may be ejected. The assay plate (1210) may further include a structure to which the assay controlling device (1205) may interact with the assay plate (1210) to move the assay plate (1210) relative to the die (104) of the cassette (100, 200). The assay controlling device (1205) may be utilized in any data processing scenario including, stand-alone hardware, mobile applications, through a computing network, or combinations thereof. Further, the assay controlling device (1205) may be used in a computing network, a public cloud network, a private cloud network, a hybrid cloud network, other forms of networks, or combinations thereof. To achieve its desired functionality, assay controlling device (1205) comprises various hardware components. Among these hardware components may be a number of controllers (1215), a number of data storage devices (1240), a number of peripheral device adapters (1225), and a number of network adapters (1230). These hardware components may be interconnected through the use of a number of busses (1260) and/or network connections. In one example, the controllers (1215), data storage devices (1240), peripheral device adapters (1225), and network adapters (1230) may be communicatively coupled via a bus (1260).

The controllers (1215) may include the hardware architecture to retrieve executable code from the data storage devices (1240) and execute the executable code. The executable code may, when executed by the controllers (1215), cause the controllers (1215) to implement at least the functionality of sending signals to the die (104) of the cassette (100, 200) and eject an amount of fluid into an assay plate (1210) according to the methods of the present specification described herein. In the course of executing code, the controllers (1215) may receive input from and provide output to a number of the remaining hardware units.

The data storage devices (1240) may store data such as executable program code that is executed by the controllers (1215) or other processing device. As will be discussed, the data storage devices (1240) may specifically store computer code representing a number of applications that the controller (1215) executes to implement at least the functionality described herein.

The data storage devices (1240) may include various types of memory modules, including volatile and nonvolatile memory. For example, the data storage devices (1240) of the present example includes Random Access Memory (RAM) (1245), Read Only Memory (ROM) (1250), and Hard Disk Drive (HDD) memory (1255). Many other types of memory may also be utilized, and the present specification contemplates the use of many varying type(s) of memory in the data storage devices (1240) as may suit a particular application of the principles described herein. In certain examples, different types of memory in the data storage devices (1240) may be used for different data storage purposes. For example, in certain examples the controllers (1215) may boot from Read Only Memory (ROM) (1250), maintain nonvolatile storage in the Hard Disk Drive (HDD) memory (108), and execute program code stored in Random Access Memory (RAM) (1245).

The data storage devices (1240) may comprise a computer readable medium, a computer readable storage medium, or a non-transitory computer readable medium, among others. For example, the data storage devices (1240) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that may contain, or store computer usable program code for use by or in connection with an instruction execution system, apparatus, or device. In another example, a computer readable storage medium may be any non-transitory medium that may contain, or store a program for use by or in connection with an instruction execution system, apparatus, or device.

The hardware adapters (1225, 1130) in the assay controlling device (1205) enable the controllers (1215) to interface with various other hardware elements, external and internal to the assay controlling device (1205). For example, the peripheral device adapters (1225) may provide an interface to input/output devices, such as, for example, a display device, a mouse, or a keyboard. The peripheral device adapters (1225) may also provide access to other external devices such as an external storage device, a number of network devices such as, for example, servers, switches, and routers, client devices, other types of computing devices, and combinations thereof.

The display device (1235) may be provided to allow a user of the assay controlling device (1205) to interact with and implement the functionality of the assay controlling device (1205). The peripheral device adapters (1225) may also create an interface between the controllers (1215) and the display device (1235), a printer, or other media output devices. The network adapter (1230) may provide an interface to other computing devices within, for example, a network, thereby enabling the transmission of data between the assay controlling device (1205) and other devices located within the network.

The assay controlling device (1205) may, when executed by the controllers (1215), display the number of graphical user interfaces (GUIs) on the display device (1235) associated with the executable program code representing the number of applications stored on the data storage devices (1240). Examples of display devices (1235) include a computer screen, a laptop screen, a mobile device screen, a personal digital assistant (PDA) screen, and a tablet screen, among other display devices (1235). Examples of the GUIs displayed on the display device (1235), will be described in more detail below.

The assay controlling device (205) further comprises a number of modules used in the implementation of the methods described herein. The various modules within the assay controlling device (1205) comprise executable program code that may be executed separately. In this example, the various modules may be stored as separate computer program products. In another example, the various modules within the assay controlling device (1205) may be combined within a number of computer program products; each computer program product comprising a number of the modules.

Figure 13:
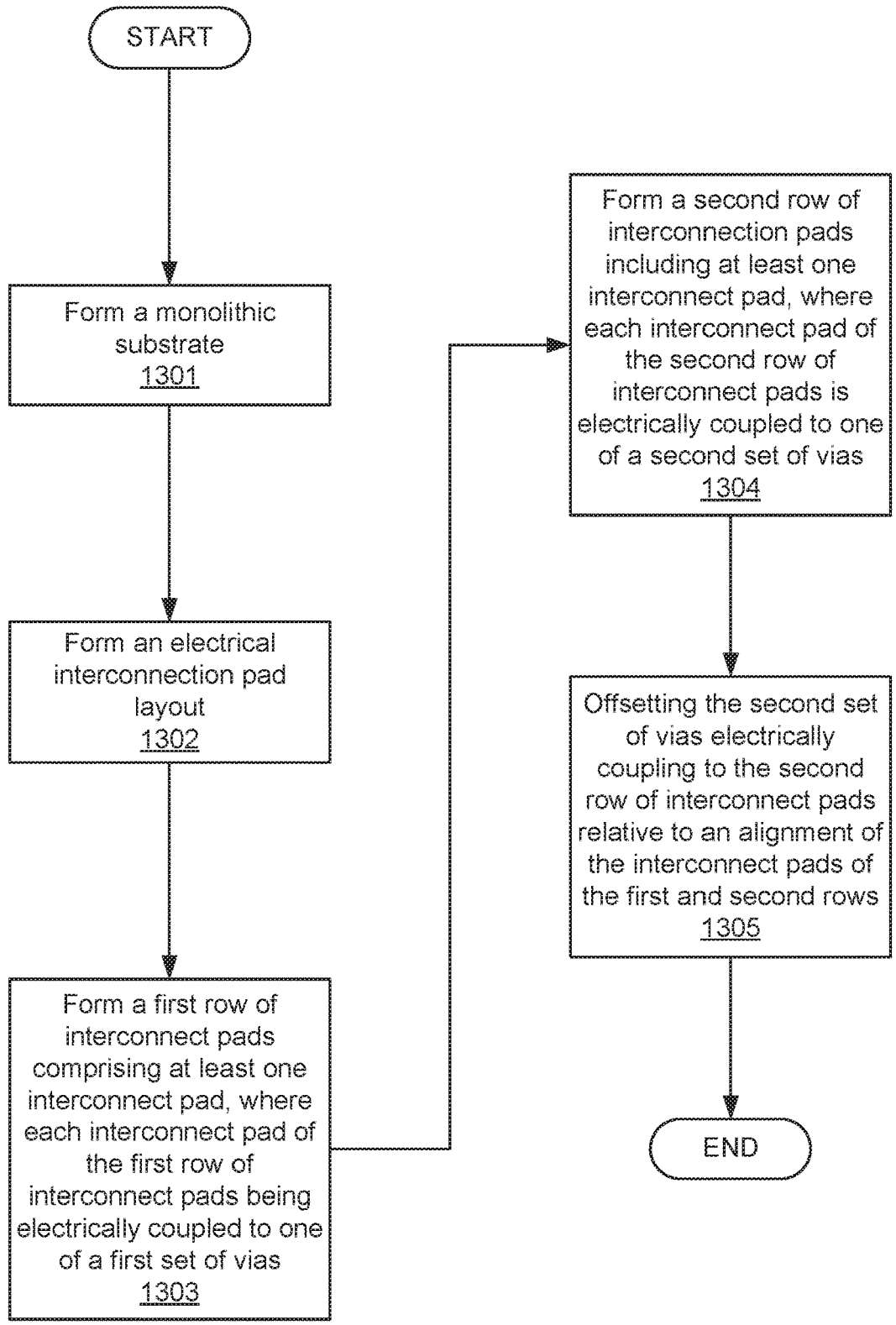
FIG. 13 is a flow chart depicting a method of forming a cassette, according to another example of the principles described herein.

FIG. 13 is a flow chart depicting a method of forming a cassette, according to another example of the principles described herein. The method of FIG. 13 may begin by forming (block 1301) a monolithic substrate (101). An electrical interconnection pad layout (1101) may be formed (block 1302) on a first side of the monolithic substrate (101). The electrical interconnection pad layout (1101) may be formed (block 1302) by forming (block 1303) a first row (116) of interconnect pads including at least one interconnect pad (105), where each interconnect pad (105) of the first row (116) of interconnect pads (105) being electrically coupled to one of a first set (126) of vias (106). Further, the electrical interconnection pad layout (1101) may be formed (block 1302) by forming (block 1304) a second row (115) of interconnection pads (105) including at least one interconnect pad (105), where each interconnect pad (105) of the second row (115) of interconnect pads (105) is electrically coupled to one of a second set (125) of vias (106). Further, the electrical interconnection pad layout (1101) may be formed (block 1302) by offsetting (block 1305) the second set (125) of vias (106) electrically coupling to the second row (115) of interconnect pads (105) relative to an alignment of the interconnect pads (105) of the first and second rows (115, 116).

The method of FIG. 13 may further include forming at least one contact seat (111) into at least one interconnect pad (105) of the first row (116) of interconnect pads (105). Further, the method of FIG. 13 may further include defining a number of electrical traces (107) on a second side of the monolithic substrate (101) electrically coupling a die (104) to the first and second sets (125, 126) of vias (106). In one example, the number of electrical traces (107) may be defined using a laser direct structuring (LDS) process.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general-purpose computer, special purpose computer, or other programmable data processing apparatus to produce a machine, such that the computer usable program code, when executed via, for example, the controller (1215) of the assay controlling device (1205) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The specification and figures describe a cassette and associated methods of forming the cassette. The cassette may include a substrate, a die coupled to the substrate, and an electrical interconnection pad layout formed on a first side of the substrate. The electrical interconnection pad layout may include a first row of interconnect pads including at least one interconnect pad. Each interconnect pad of the first row of interconnect pads may be electrically coupled to one of a first set of vias. The electrical interconnection pad layout may also include a second row of interconnection pads including at least one interconnect pad. Each interconnect pad of the second row of interconnect pads being electrically coupled to one of a second set of vias. The second set of vias electrically coupled to the second row of interconnect pads are offset relative to an alignment of the interconnect pads of the first and second rows.

The preceding description has been presented to illustrate and describe examples of the principles described. This description is not intended to be exhaustive or to limit these principles to any precise form disclosed. Many modifications and variations are possible in light of the above teaching.

What is claimed is:

1. A cassette comprising:
    a substrate;
    a die coupled to the substrate; and
    an electrical interconnection pad layout formed on a first side of the substrate comprising:
        a first row of interconnect pads comprising at least one interconnect pad, each interconnect pad of the first row of interconnect pads being electrically coupled to one of a first set of vias; and
        a second row of interconnection pads comprising at least one interconnect pad, each interconnect pad of the second row of interconnect pads being electrically coupled to one of a second set of vias,
    wherein the second set of vias electrically coupled to the second row of interconnect pads are offset relative to an alignment of the interconnect pads of the first and second rows.

2. The cassette of claim 1, further comprising a number of electrical traces formed on a second side of the substrate, wherein the first and second sets of vias electrically couple the electrical interconnection pad layout to the electrical traces, and wherein the offset of the second set of vias electrically coupled to the second row of interconnect pads creates an offset of the electrical traces formed on a second side of the substrate.

3. The cassette of claim 1, wherein at least one of the interconnect pads of the first row of interconnect pads comprises a contact seat defined therein, the contact seat to allow for the seating of a pogo connection.

4. The cassette of claim 1, wherein at least one of the interconnect pads of the second row of interconnect pads comprises a fire interconnect pad.

5. A system for ejecting a fluid into an assay comprising:
a printed circuit assembly (PCA) comprising:
   at least one pogo connector; and
at least one dispense head, the at least one dispense head comprising:
   a substrate;
   a die coupled to the substrate; and
   an electrical interconnection pad layout formed on a first side of the substrate comprising:
      a first row of interconnect pads comprising at least one interconnect pad, each interconnect pad of the first row of interconnect pads being electrically coupled to one of a first set of vias; and
      a second row of interconnection pads comprising at least one interconnect pad, each interconnect pad of the second row of interconnect pads being electrically coupled to one of a second set of vias,
   wherein the second set of vias electrically coupled to the second row of interconnect pads are offset relative to an alignment of the interconnect pads of the first and second rows.

6. The system of claim 5, wherein at least one of the interconnect pads of the second row of interconnect pads comprises a fire interconnect pad.

7. The system of claim 5, wherein at least one of the interconnect pads of the first row of interconnect pads comprises a contact seat defined therein, the contact seat to allow for the seating of the at least one pogo connector therein when the at least one dispense head interfaces with the PCA.

8. The system of claim 5, wherein the first row of interconnect pads comprises at least a ground interconnect pad, a source voltage interconnect pad, and a thermal sense resistor (TSR) interconnect pad.

9. The system of claim 8, wherein the second row of interconnect pads comprise at least a fire interconnect pad, a clock interconnect pad, and a data interconnect pad.

10. The system of claim 5, wherein the PCA interfaces with the electrical interconnection pad layout of the at least one dispense head by sliding the at least one pogo connector over the second row of interconnect pads and electrically coupling the at least one pogo connector to at least one interconnect pad of the first row of interconnect pads.

11. The system of claim 5, wherein the PCA interfaces with the electrical interconnection pad layout of the at least one dispense head by dropping the at least one pogo connector onto at least one interconnect pad in the first or second rows of interconnect pads in a direction perpendicular to a plane formed by the electrical interconnection pad layout.

12. A method of forming a cassette comprising:
forming a monolithic substrate;
forming an electrical interconnection pad layout formed on a first side of the monolithic substrate by forming:
   a first row of interconnect pads comprising at least one interconnect pad, each interconnect pad of the first row of interconnect pads being electrically coupled to one of a first set of vias; and
   a second row of interconnection pads comprising at least one interconnect pad, each interconnect pad of the second row of interconnect pads being electrically coupled to one of a second set of vies; and
offsetting the second set of vias electrically coupling to the second row of interconnect pads relative to an alignment of the interconnect pads of the first and second rows.

13. The method of claim 12, further comprising forming at least one contact seat into at least one interconnect pad of the first row of interconnect pads.

14. The method of claim 12, further comprising defining a number of electrical traces on a second side of the monolithic substrate electrically coupling a die to the first and second sets of vias.

15. The method of claim 12, wherein the number of electrical traces are defined using a laser direct structuring (LDS) process.

* * * * *